United States Patent [19]

Musacchio et al.

[11] Patent Number: 4,694,010

[45] Date of Patent: Sep. 15, 1987

[54] ANTICONVULSANT COMPOSITIONS AND METHOD

[75] Inventors: Jose M. Musacchio, New York, N.Y.; Frank C. Tortella, Columbia, Md.

[73] Assignee: New York University, New York, N.Y.

[21] Appl. No.: 766,838

[22] Filed: Aug. 16, 1985

[51] Int. Cl.$^4$ .................... A61K 31/44; A61K 31/415
[52] U.S. Cl. .................................. 514/304; 514/386; 514/389
[58] Field of Search ........................ 514/380, 304, 389

[56] References Cited

PUBLICATIONS

Chem. Abst. (1984) 16449H.
High-Affinity DM Binding Sites in Guinea Pig Brain, Craviso, G. L. and Musacchio, J. M. *Mol. Pharmacol.*, 23: 619–628 (1982).
High-Affinity DM Binding Sites in Guinea Pig Brain, Craviso, G. L. and Musacchio, J. M., *Mol. Pharmacol.*, 23: 629–640 (1982).

*Primary Examiner*—Stanley J. Friedman
*Attorney, Agent, or Firm*—Darby & Darby

[57] ABSTRACT

Diphenylhydantoin and for dextromethorphan to control seizures.

26 Claims, 4 Drawing Figures

ANTICONVULSANT COMPOSITIONS AND METHOD

FIELD OF THE INVENTION

This invention relates to a group of novel compositions containing diphenylhydantoin and/or dextromethorphan or another compound that binds to the same sites in the brain as dextromethorphan, with substantially the same or higher affinity. Another aspect of this invention relates to the use of these compositions as anticonvulsants, and to methods for controlling seizures using these compositions.

BACKGROUND OF THE INVENTION

Most types of epileptic seizures, including induced generalized or focal seizures, except absence seizures, can be treated and prevented with diphenylhydantoin (DPH), which is also commonly called phenytoin, and other antiepileptic hydantoins.

DPH has the following structural formula

DPH usually exerts antiepileptic activity without causing general depression of the central nervous system. It can limit the development of maximal seizure activity and reduce the spread of the seizure process from an active focus.

Antiepileptic preparations containing DPH (and other antiepileptic hydantoins) are available in solid (oral) and liquid (oral and injectable) forms; they contain from 30 to 250 mg of DPH per unit dose.

The effectiveness of DPH increases with dosage. However, DPH is also toxic. Most of its toxic effects increase with dosage, length of exposure, and vary with the mode of administration.

Dose-dependent toxic effects associated with chronic use of DPH and other hydantoins include cerebellar vestibular effects (nystagmus, ataxia, diplopia, vertigo, etc.) and other central nervous system disturbances (blurred vision, mydriasis, hyperactive tendon reflexes, etc.), behavioral changes (hyperactivity, confusion, dullness, drowsiness and hallucinations), increased frequency of seizures, peripheral neuropathy, gastrointestinal distress, gingival hyperplasia, osteomalacia, megaloblastic anemia (that can be fatal), hirsutism, endocrine effects, lymphadenopathy et al. At very high doses (especially when administered intravenously), DPH can also cause cardiovascular collapse and/or general depression of the central nervous system.

DPH is not the only antiepileptic drug. A variety of other antiepileptic agents are known. Unfortunately, many of them also have undesirable toxic and side effects. Moreover, most known antiepileptic agents are effective for only selective types of seizures.

Accordingly, there is a need in the field for development of an anticonvulsant agent that would cause as few and as mild toxic and side effects as possible and yet be effective against a wide variety of seizure types. More specifically, there is a need for an anticonvulsant agent that would be effective at doses that minimize dose-related side effects against a variety of seizures.

In Mol. Pharmacol., 23:619-628 and 23:629-640 (1983) Craviso, G. L. and Musacchio, J. M. reported that dextromethorphan (DM), a nonnarcotic, nonaddictive, antitussive agent, had distinct binding sites in the cental nervous system, which were different from the binding sites for opiate compounds. The same investigators found that the binding of DM was effectively inhibited in vitro by a number of nonnarcotic centrally active antitussives (including certain DM analogs), certain phenothiazine neuroleptics, as well as some other compounds such as selective antidepressants, antihistamines, and muscarinic agents (i.e. agents that bind to the muscarinic receptor). They also found that the in vitro binding of DM to the central nervous system was markedly increased in the presence of certain compounds such as DPH and noscapine, but they were unable to predict which compounds would enhance DM binding and which would not. The authors proposed that research be conducted to determine whether DPH is an antitussive (or whether DM is an anticonvulsant), but that statement is at best a proposal for experimentation and does not suggest the method or the compositions of the present invention. Specifically, the anticonvulsant activity of DM can not be deduced or suggested from the disclosure of these references. In addition, the fact that DPH increases the binding of DM does not suggest that one would potentiate activity of the other, much less that DM would potentiate DPH activity.

It has now been discovered that DM and several other compounds that bind to the same sites in the brain possess substantial anticonvulsant activity in vivo. More important, it has been unexpectedly discovered that DM and these other compounds vigorously potentiate the anticonvulsant activity of DPH in vivo when administered simultaneously (or consecutively) with DPH. As a result, the minimum effective dose of DPH (and consequently its dose-dependent side-effects) can be substantially decreased. The potentiating effect is present even at subthreshold levels of DM (or the other compounds that bind to the same CNS sites).

Dextromethorphan (D-3-methoxy-N-methylmorphinan) has the following structural formula:

It is sold as an antitussive in various liquid, resin, and solid antitussive dosage forms containing from 5 to 30 mg/5 ml of DM (or the equivalent), together with alcohol and/or other carriers and active ingredients used in management of cough and other symptoms of the common cold.

Although DM is a potent antitussive, it has no analgesic or addictive properties. Unlike codeine to which it is structurally related, it rarely produces drowsiness or gastrointestinal disturbances and has low toxicity (Goodman & Gilman's, The Pharmacological Basis of Therapeutics, Sixth Ed., MacMillan Publishing Co., New York 1980).

Therefore, use of DM (and other relatively innocuous compounds that compete with DM for the same CNS binding sites) to potentiate DPH will result in a substantial decrease in the dose-and exposure-dependent side effects of DPH with a concomitant enhancement (or without a compromise) in anti-seizure activity.

OBJECTS OF THE INVENTION

Accordingly, it is an object of this invention to provide a method for controlling seizures in mammals, and particularly clinical epileptic seizures.

Another object of this invention is to provide pharmaceutical formulations comprising an effective amount of anti-convulsant agents useful for inhibiting, preventing, or controlling epileptic seizures.

Another object of the invention is to provide pharmaceutical compositions that have anticonvulsant activity similar or superior to that of DPH, at lower doses than DPH, said compositions having substantially less toxicity and fewer side effects than DPH.

These and other objects of the invention will be apparent to one of ordinary skill in the art in light of the present description, appended claims and accompanying drawings.

SUMMARY OF THE INVENTION

One aspect of the present invention is directed to an anticonvulsant composition comprising as an active ingredient an amount of a compound selected from the group consisting of dextromethorphan and non-narcotic, nonaddictive, low-toxicity compounds that bind to the same central nervous system sites as dextromethorphan with at least about the same affinity for said sites, said amount being effective for controlling seizures in mammals.

Another aspect of the present invention is directed to an anticonvulsant composition comprising as active ingredients (a) an antiepileptic hydantoin or noscapine, and (b) a compound selected from the group consisting of dextromethorphan and other non-narcotic, nonaddictive, low-toxicity compounds that bind to the same central nervous system sites as dextromethorphan with at least about the same affinity for said sites; wherein the amount of the active ingredients in combination is effective for controlling seizures in mammals, and the amount of said compound is at least sufficient to potentiate said hydantoin or noscapine.

Still other aspects of the present invention are directed to dosage forms comprising amounts of the aforementioned compositions effective for controlling seizures in mammals.

Yet another aspect of the present invention relates to a method for controlling seizures in a mammal in need of such treatment comprising administering to said mammal an amount effective for controlling seizures of a compound selected from the group consisting of dextromethorphan and non-narcotic, nonaddictive, low-toxicity compounds that bind to the same sites in the central nervous system as dextromethorphan with at least about the same affinity for said sites as dextromethorphan.

Another aspect of the present invention relates to a method for controlling seizures in a mammal in need of such treatment comprising administering to said mammal an amount of an antiepileptic hydantoin (or noscapine) and an amount of dextromethorphan or another non-narcotic, nonaddictive, low-toxicity compound that binds to the same central nervous system sites as dextromethorphan with at least about the same affinity, said amounts in combination being effective for controlling seizures in said mammals, said amount of DM or said other compound being at least sufficient to potentiate DPH.

DETAILED DESCRIPTION OF THE INVENTION

The present inventors have discovered that the nonopiate antitussive DM and several other compounds that bind to the same central nervous system (CNS) site as DM with with at least about the same affinity are effective anticonvulsant agents and also potentiate the anticonvulsant action of DPH and other antiepileptic hydantoins, thus substantially lowering the minimum effective dose of DPH, and the other hydantoins. As a result, the amount of hydantoin necessary for antiepileptic activity in a given case is substantially lower than that which would have been effective for the same purpose, if the hydantoin had been used alone.

Any one of a number of nonaddictive, nonnarcotic compounds of low toxicity that effectively compete with DM for the same central nervous system binding sites could be used to potentiate DPH. Such compounds include but are not limited to non-opiate antitussives that bind to the same CNS sites as DM. Specific examples of compounds that can be used in the compositions of the present invention include benztropine, chlorpromazine, perphenazine, fluphenazine, trifluoperazine, prochlorperazine, alpha-flupenthixol, trimeprazine, dimethoxanate, opipramol, promethazine, pipazethate, carbetapentane, caramiphen, and noscapine as well as pharmaceutically acceptable derivatives, homologs, isomers, analogs and organic and inorganic addition salts thereof having therapeutic activity as provided herein. For example, the DM analogs that have the groups-$CH_2(CO)CH_3$ and $CH_2CH(CH_3)OH$ instead of $CH_3$ as N-position substituents can be used. The methylsulfonate salt of benztropine, the hydrochloride and ethanedisulfonate salts of caramiphen, the citrate salt of carbetap-entane, the maleate and hydrochloride salts of chlorpromazine, the dihydrochloride salt of flupenthixol and fluphenazines are some examples of the forms of the above compounds that can be used in the compositions of the present invention.

Preferred are perphenazine, fluphenazine, trifluoperazine, opipramol, and carbetapentane with DM being most preferred. These compounds have anticonvulsant activity independent of their DPH-potentiating action.

The structural formulas and IUPAC names of these compounds are given in Table I below.

TABLE I benztropine: 3-(diphenylmethoxy)-8-methyl-8-azabicyclo[3.2.1]octane caramiphen: 1-phenylcyclopentanecarboxylic acid 2-(diethylamino)ethyl ester carbetapentane: 1-phenylcyclopentanecarboxylic acid 2-(2-diethylaminoethoxy)ethyl ester chlorpromazine: 2-chloro-N,N—dimethyl-10H—phenothiazine-10-propanamine dimethoxanate: 10H—phenothiazine-10-carboxylic acid 2-[2-(dimethylamino)ethoxy]ethyl ester flupenthixol: 4-[3-[2-(trifluoromethyl)-9H—thioxanthen-9-ylidene]propyl]-1-piperazineethanol fluphenazine: 4-[3-[2-(trifluoromethyl)-10H—phenothiazin-10-yl]propyl]-1-piperazineethanol opipramol: 4-[3-(5H—dibenz[b,f]azepin-5-yl)propyl]-1-piperazineethanol

TABLE I-continued perphenazine: 4-[3-(2-chlorophenothiazin-10-yl)propyl]-1-piperazineethanol pipazethate: 10H—pyrido[3,2-b][1,4]benzothiadiazine-10-carboxylic acid 2-(2-piperidinoethoxy)ethyl ester prochlorperazine: 2-chloro-10-[3-(4-methyl-1-piperazinyl)propyl]-10H—phenothiazine promethazine: N,N,alpha-trimethyl-10H—phenothiazine-10-ethanamine trifluoperazine: 10-[3-(4-methylpiperazin-1-yl)-propyl]-2-(trifluoromethyl)-10H—phenothiazine trimeprazine: 10-[3-(dimethylamino)-2-methylpropyl]phenothiazine

TABLE I-continued noscapine: 6,7-dimethoxy-3-(5,6,7,8-tetrahydro-4-methoxy-6-methyl-1,3-dioxolo[4,5-g]isoquinolin-5-yl)-1(3H)—isobenzofuranone The above compounds can be obtained from commercial sources such as:
DPB: Polychemicals Laboratories, Bronx, N.Y.
DM: Hoffmann-La Roche, Nutley, N.J.
benztropine: Merck Sharp and Dohme, West Point, Pa.
carbetapentane: CM/K&K Life Sciences Group, Cleveland, Ohio
flupenthixol: Smith Kline French, Philadelphia, Pa.
opipramol: Ciba-Geigy, Summit, N.J.
mephenytoin: Sandoz Pharmaceuticals, Inc., East Hanover, N.J.
ethotoin: Abbott Laboratories, North Chicago, Ill.
noscapine: Mallincrodt Pharmaceutics, St. Louis, Mo.
or can be synthesized using well-known techniques, such as described in U.S. Pat. Nos. 2,409,754; 2,595,405; Swiss Pat. No. 234,452; British Pat. No. 753,799; U.S. Pat. Nos. 2,404,588; 2,645,640; 2,778,824; British Pat. No. 925,538; U.S. Pat. No. 3,194,733; Swiss Pat. Nos. 359,143 and 360,061; U.S. Pat. Nos. 2,860,138; 2,989,529; 2,902,484; 2,530,451 and 2,607,773; 2,921,069; 2,837,518; 2,676,177; and 3,108,106, the disclosure of which is incorporated by reference herein. In addition to DPH, other antiepileptic hydantoins can be advantageously potentiated by DM and compounds that bind to the same brain sites. These include mephenytoin, N-demethylated mephenytoin, and ethotoin. However, DPH is preferred.

The compositions of the present invention can be administered orally or parenterally (subcutaneously or intravenously because intramuscular injection is not indicated for DPH-containing compositions).

In the case of potentiated DPH compositions, it is not essential that DPH and the potentiating compound be administered simultaneously or in the same dosage form. Sequential administration is acceptable. However, simultaneous administration is preferred.

The active ingredients in the oral dose are preferably administered in the form of a tablet, pill, capsule or other solid dosage unit. Coating of the tablet or protective capsule is desirable to facilitate swallowing or to prevent unpleasant taste. Suitable coatings may be prepared from aqueous suspension containing sugar and insoluble powders such as starch, calcium carbonate, talc or titanium dioxide suspended with a suitable mixing agent such as gelatin. Film coatings consisting of water-soluble or dispersable materials such as hydroxypropylmethylcellulose, cellulose, methylcellulose, carboxymethylcellulose, and mixtures of cellulose acetate phthalate and polyethylene glycol applied out of aqueous or nonaqueous solvents are suitable for coating the tablets and pills made according to the present invention. Soft shell gelatin capsules of the type normally used as pharmaceutical coatings are also suitable as dosage forms for the invention. Of course, the capsules may comprise any well-known pharmaceutically acceptable material such as gelatin, cellulose derivatives or the like.

The active ingredients of the present invention may be compounded in the desired oral form in combination with inert ingredients including fillers such as talc, lactose, starch, bentonite, diatomaceous earth, lubricants and food flavorings. Tablets for use in the present invention may be made by punching or compressing the active ingredients and the fillers in a tabletting machine.

Liquid oral doses in the form of solutions and suspensions are also suitable for use in the present invention as are suppositories for rectal administration. In making solutions and suspensions, the active ingredients may be dissolved or suspended in distilled water containing a small amount of alcohol to facilitate hydantoin suspension, conventional U.S. Pat. syrup formulations and any other pharmaceutically acceptable carrier liquid.

For parenteral administration the compounds of the invention are dissolved in a pharmaceutically acceptable injectable carrier liquid. A preferred carrier liquid for DPH includes polypropylene glycol and alcohol in water (pH:12 by addition of NaOH) and would be a suitable carrier for the potentiated compositions of the present invention.

When used as anticonvulsants in mammals, the compositions of the present invention containing DM (or one or more of the compounds that bind to the same site) can generally be administered at a dosage level from about 15 to about 200 milligrams and preferably from about 30 to about 150 milligrams of active ingredient two or three times a day.

The potentiated compositions containing DPH can generally be administered at a dosage level of DPH ranging from about 50 to about 500 mg per day for adults (preferably about 100 to 300 mg) and from about 1 to about 8 mg of DPH per kg body weight/day for children.

In these potentiated DPH-containing compositions, the amount of DPH necessary for effectiveness is usually substantially lower than it would have been if DPH had been used alone to control the epilepsy. The amount of the potentiating compound should be at least sufficient to potentiate the DPH, i.e. at least sufficient to lower the minimum effective dose of DPH. The noscapine doses are comparable to the ones given for DPH.

Although subthreshold levels of the potentiating compound have sufficient potentiating activity when used in conjunction with DPH, the potentiated compositions of the present invention are not limited to containing subthreshold levels of the potentiating compound.

The daily effective dosage, or the dosage required to prevent or inhibit or control convulsions from a particular disease or stimulant depends on the condition being treated, the individual characteristics of each mammal being treated and the nature of the physical or chemical stimulus inducing or responsible for the convulsive activity. Thus, the exact dose required to alleviate convulsions attributable to a particular disorder or stimulus or their effects will vary within the range discussed above from one patient to another and is subject to optimization, which can be carried out by conventional and convenient experimental techniques.

Solid pharmaceutical dosage forms such as pills, capsules, or tablets may contain from about 40 to 300 milligrams of active ingredient, or combination of active ingredients. More specifically, such dosage forms may contain from about 15 to 200 mg of DM (or other potentiating compound) and from about 25 to 100 mg of DPH (or other hydantoin).

The liquid oral dosage forms of the present invention are preferably administered in the form of a solution or suspension in a pharmaceutically acceptable vehicle. Liquid dosages containing from about 9 to about 60 milligrams of active ingredient (or combination of active ingredients) per cubic centimeter of vehicle are useful in administering these agents to mammals.

The liquid parenteral dosage forms of the present invention may contain from about 9 to about 60 mg/of active ingredient or combination of active ingredients per ml of vehicle.

Suppository dosage forms may be prepared by incorporating an active agent into a base material that can be formed into the desired shape. Suitable base materials include cocoa butter, glycerinated gelatin, hydrogenated vegetable fats, mixtures of polythethylene glycols of various molecular weights and fatty acid esters of polyethylene glycol. Suppositories for adults may contain from about 40 to about 300 milligrams of active ingredient or combination of active ingredients.

The invention is further described below by reference to specific examples, which are intended to illustrate the invention without limiting its scope.

EXAMPLES

The anticonvulsant activity of the instant compositions was measured by inducing maximal electroshock seizures (MES) in rats using the following standard testing conditions:

Animals. Male, Sprague Dawley rats (200–300 g from Zivic Miller, Alison Park, Pa.) were used for all experiments. Upon delivery, the animals were housed individually in a temperature-controlled room with a standard 12-hour light-dark cycle (lights on 0600 hr to 1800 hr). Food and water were available ad libitum.

Maximal electroshock seizures (MES). Supramaximal (tonic extension of the hindlimbs) seizures were induced electrically by means of a Wahlquist shock apparatus (Wahlquist Inst., Salt Lake City, Utah) with a built-in high internal resistance designed to provide a constant current across animals A 60-Hz, 50 mA current was delivered transauriculy for 2.0 seconds via small alligator clips attached to the pinna of each ear. This current intensity elicited complete tonic extension of the hindlimbs in at least 90% of control rats. Two measures of seizure severity were recorded for each MES seizure; the duration of tonic forelimb extension (TFE) and the presence or absence of tonic hindlimb extension (THE). For the MES test, rats were placed in a clear rectangular plastic cage (45×25×12 cm) with the top open, permitting full view of the animals' motor response to the seizure.

In preliminary studies ethosuximide (400 mg/kg, s.c.) a drug which is known to prevent tonic extension of maximal tonic extension threshold seizures but is ineffective against MES seizures (Piredda et al, 1985 *J. PET* 232:741 (1985), was also found ineffective against MES seizures in these Examples. Therefore, the shock parameters used here clearly induce MES, and not threshold, seizures. Throughout the study, all animals were used only once.

Experimental protocol. Each rat received a single subcutaneous (s.c.) injection of dextromethorphan (DM, n=10 per group) or diphenylhydantoin (DPH, n=10 per group). At various times postinjection, the animals were subjected to an MES seizure and tested as described above. The duration of action for each drug was determined over a two-hour time period. Dose-response studies for DM (15, 20, 25, and 30 mg/kg) and DPH (3.125, 6.25, 12.5, 25.0, and 50 mg/kg) were subsequently carried out at the time of maximal effect, i.e. 30 minutes postinjection. In separate groups of rats, a subthreshold effective dose of DM (15 mg/kg) was administered simultaneously with DPH (1.56, 3.125 and 6.25 mg/kg). Thirty minutes later the animals were exposed to a single MES seizure and their response measured The method of Litchfield and Wilcoxin *J. PET* 96:99 (1949) was used to determine the ED values and 95% confidence limits for each drug tested, as well as for the combination of DM and DPH. Potency comparisons were made using the computer program No. 10 by Tallarida and Murray (Manual of Pharmacologic Calculations, Springer Verlag, N.Y., 1981).

Figure 1:
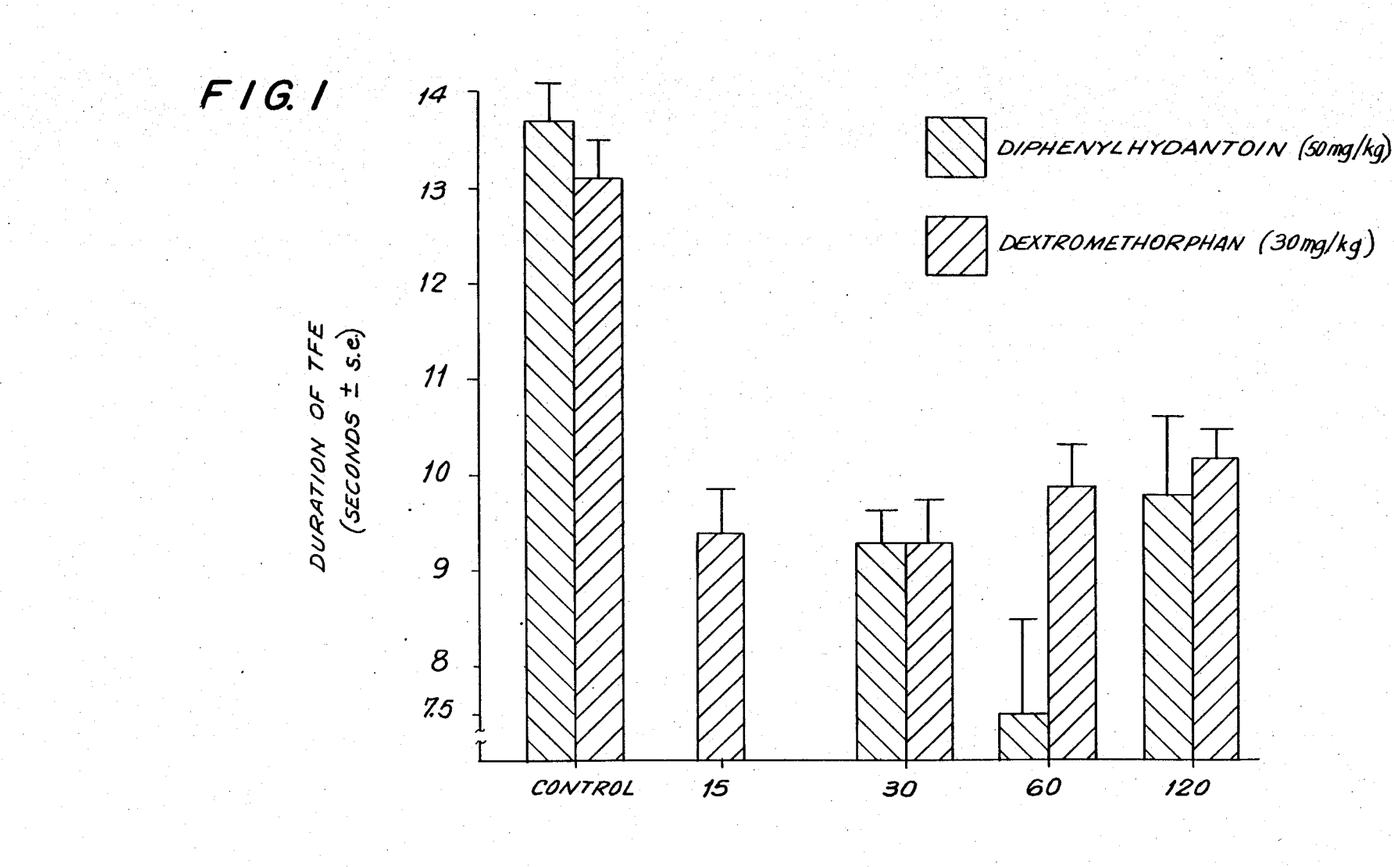
FIG. 1 is a bar diagram showing the duration of tonic forelimb extension as a function of the amount of anticonvulsant agent administered.
Figure 2:
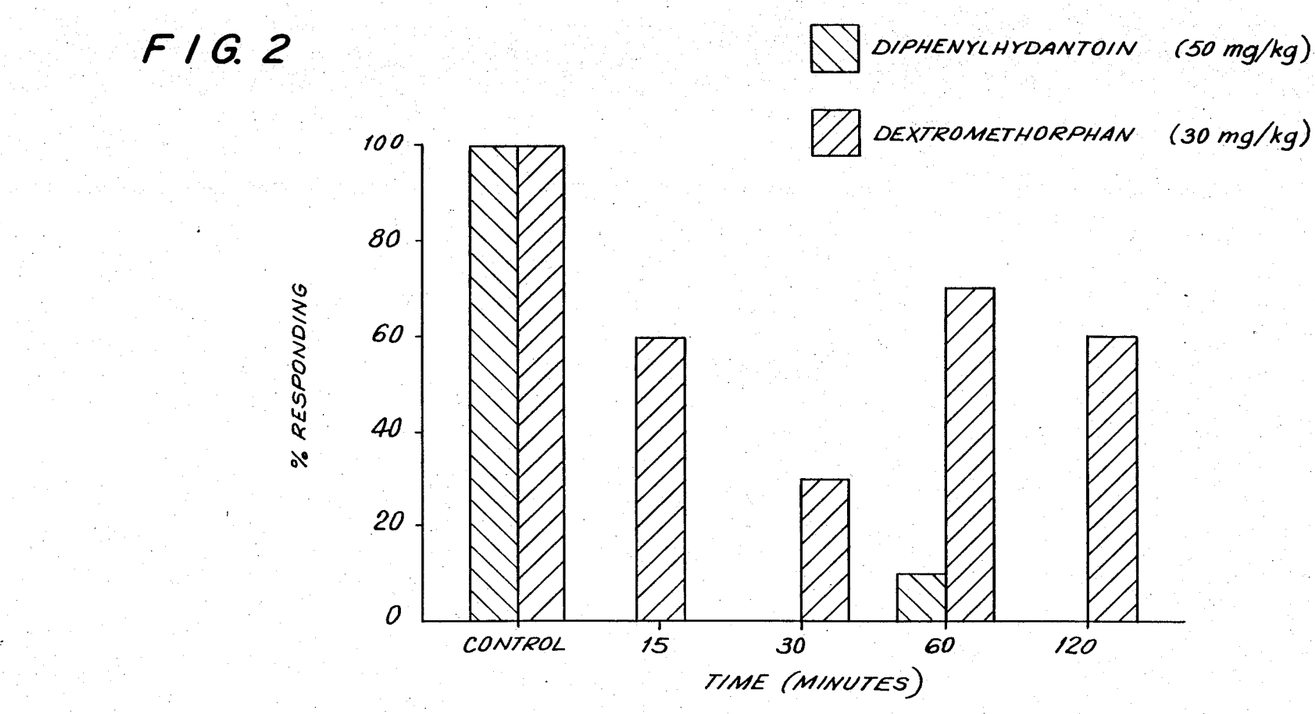
FIG. 2 is a bar diagram showing the presence of seizure activity, as a function of the amount of anticonvulsant administered.
Figure 3:
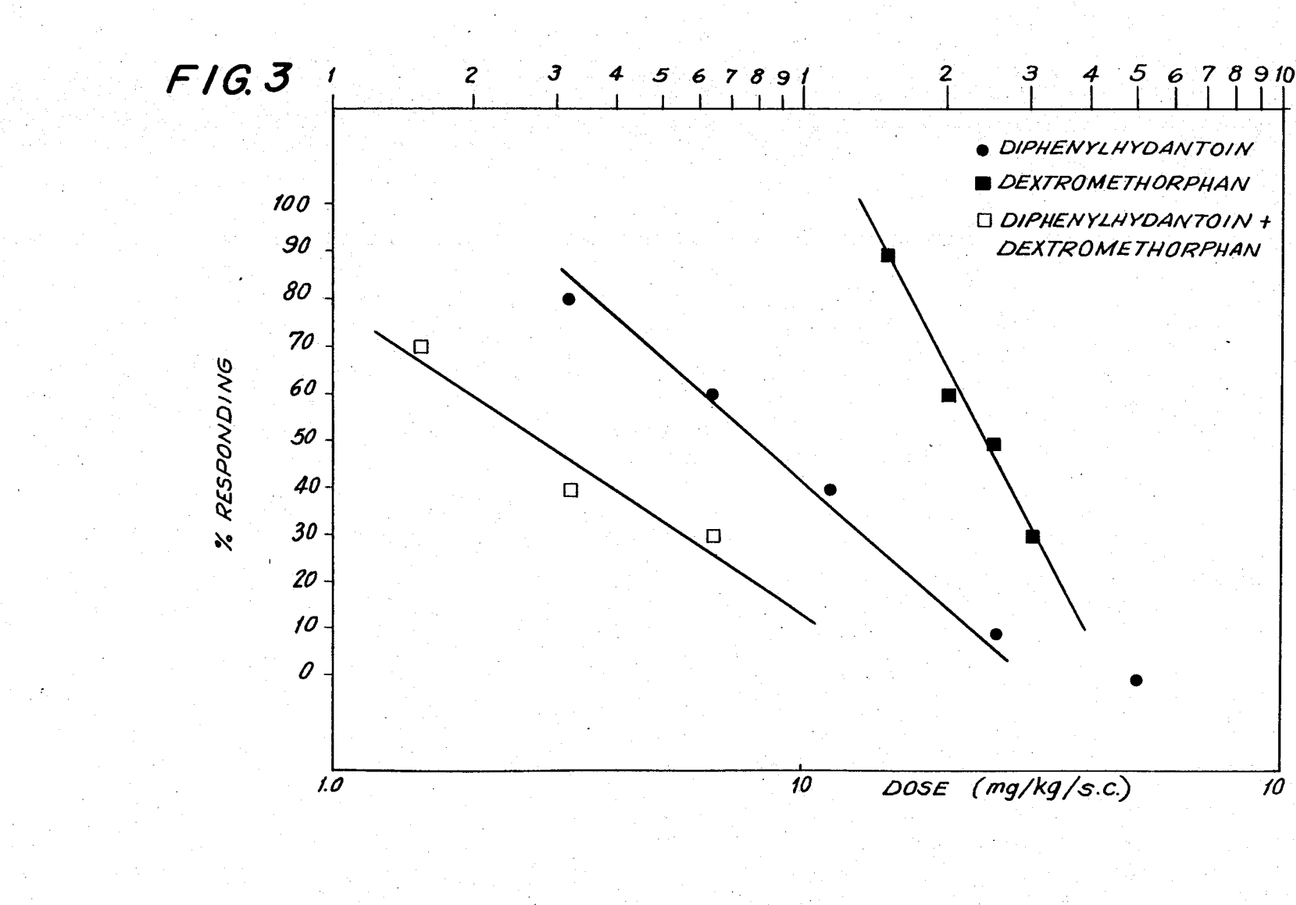
FIG. 3 is a semilog plot of the doses at which a given anticonvulsant composition controls seizure activity of a percentage of the subjects tested.
Figure 4:
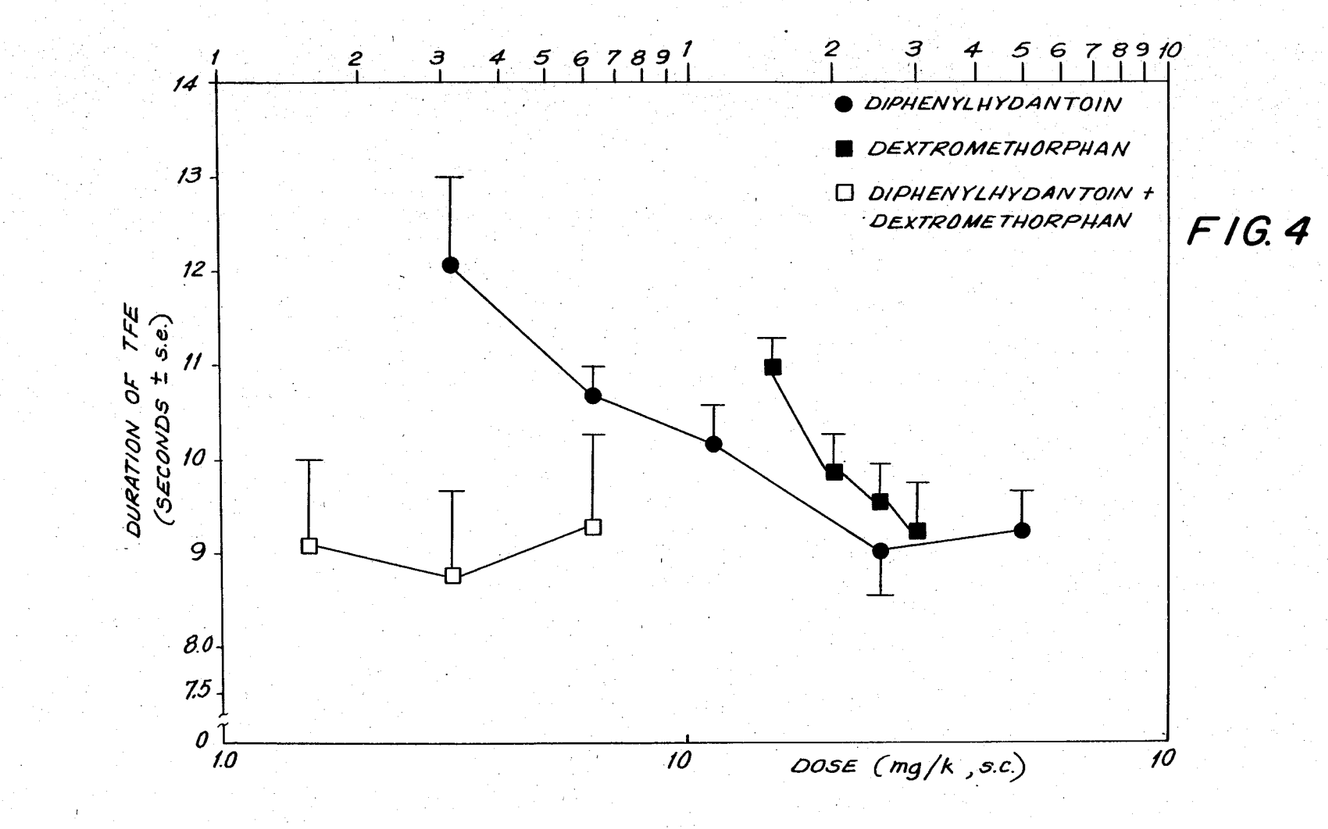
FIG. 4 is a semilog plot of the doses at which a given anticonvulsant composition limits the duration of tonic forelimb extension.

Results. The administration of DM and DPH resulted in a time-(FIGS. 1 and 2) and dose-(FIGS. 3 and 4) related decrease in the duration of TFE and blockade of THE. Maximal anticonvulsant effect occurred with 15–30 minutes following DM administration and within 30–60 minutes following the injection of DPH, with significant anticonvulsant action still evident two hours later (FIGS. 1 and 2). The anticonvulsant $ED_{50}$ (95% CL) for the effect of DM to block THE was 24.1 mg/kg (19.7–29.5) (FIG. 3). The tests show DM to be only 3 times less potent than DPH as an anticonvulsant in the rat. In addition, the simultaneous administration of a subthreshold dose of DM (15 mg/kg) increased the potency of DPH (FIGS. 3 and 4), lowering the anticonvulsant ED 50 for DPH threefold to 2.79 mg/kg (1.44–5.43) in the MES test (FIG. 3). In fact, additional preliminary tests indicate that DM is able to increase the potency of DPH more than three-fold.

At the time of testing, the DM- and DM/DPH-treated animals exhibited normal exploratory behavior when placed in the novel testing environment. There were no signs of overt sedation, ataxia or motor impairment at any time after drug administration.

The above results indicate that the co-administration of DM and DPH has a synergistic effect in that the former (even at subthreshold levels) potentiates the latter. A three-fold decrease of the $ED_{50}$ of DPH would significantly lower the incidence and severity of its side effects.

What is claimed is:

1. A method for controlling seizures in a mammal in need of such treatment comprising administering to said mammal an amount of:
    (a) an antiepileptic hydantoin; and
    (b) an antiepileptic hydantoin-potentiating amount of a compound selected from the group consisting of dextromethorphan, caramiphen and carbetapentane; said amounts in combination being effective for controlling seizures in said mammal.

2. A method according to claim 1 wherein the amount of said hydantoin is substantially lower than that which would display the same seizure-controlling activity if said hydantoin had been used as the sole active ingredient.

3. A method according to claim 1 wherein said hydantoin is selected from the group consisting of diphenylhydantoin and pharmaceutically acceptable salts thereof.

4. A method according to claim 3 wherein said compound is dextromethorphan.

5. A method according to claim 3 wherein said compound is caramiphen.

6. A method according to claim 3 wherein said compound is carbetapentane.

7. A method according to claim 3 wherein said compound is used at a subthreshold level.

8. A method according to claim 1 contained in a liquid injectable dosage form.

9. A method according to claim 1 contained in a solid oral dosage form.

10. A method according to claim 1 contained in a liquid oral dosage form.

11. A method according to any one of claims 4, 5 and 6 wherein said compound is used at a subthreshold level, and said hydantoin is dihpenylhydantoin used in an amount substantially lower than that which would display the same seizure-controlling activity if said hydantoin were used as the sole active ingredient.

12. The method of claim 1 wherein the amount of said compound is at least sufficient to potentiate said hydantoin.

13. The method of claim 1 wherein said hydantoin and said compound are co-administered.

14. The method of claim 1 wherein said hydantoin and said compound are administered successively.

15. A composition comprising as active ingredients:
  (a) an amount of a compound selected from the group consisting of diphenylhydantoin and pharmaceutically acceptable salts thereof; and
  (b) an amount of a compound selected from the group consisting of dextromethorphan, —CH$_2$(CO)CH$_3$ and —CH$_2$CH(CH$_3$)OH substituted dextromethorphan, caramiphen and carbetapentane and pharmaceutically acceptable salts thereof; said amount of said compound being at least sufficient to potentiate said hydantoin; said amounts in combination being effective for controlling seizures in a mammal in need of such treatment.

16. A composition according to claim 15, wherein the amount of said hydantoin is substantially lower than that which would display the same seizure-controlling activity if said hydantoin had been used as the sole active ingredient.

17. A composition according to claim 15 wherein said hydantoin is selected from the group consisting of diphenylhydantoin and pharmaceutically acceptable salts thereof.

18. A composition according to claim 17 wherein said compound is dextromethorphan.

19. A composition according to claim 17 wherein said compound is caramiphen.

20. A composition according to claim 17 wherein said compound is carbetapentane.

21. A composition according to claim 17 wherein said compound is used at a subthreshold level.

22. A composition according to claim 15 contained in a liquid injectable dosage form.

23. A composition according to claim 15 contained in a solid oral dosage form.

24. A composition according to claim 15 contained in a liquid oral dosage form.

25. A composition according to any one of claim 18, 19 and 20 wherein said compound is used at a subthreshold level, and said hydantoin is diphenylhydantoin used in an amount substantially lower than that which would display the same seizure-controlling activity if said hydantoin were used as the sole active ingredient.

26. A composition according to claim 15 wherein the amount of said compound is at least sufficient to potentiate said hydantoin.

* * * * *